United States Patent
Wang et al.

(10) Patent No.: US 9,605,052 B2
(45) Date of Patent: Mar. 28, 2017

(54) METHOD FOR EXTRACTING IGY (γ-LIVETIN) FROM EGG YOLK

(71) Applicant: National Taiwan Normal University, Taipei (TW)

(72) Inventors: Yu-Chie Wang, Taipei (TW); Zong-Ming Wang, Taipei (TW)

(73) Assignee: NATIONAL TAIWAN NORMAL UNIVERSITY (TW)

( * ) Notice: Subject to any disclaimer, the term of this patent is extended or adjusted under 35 U.S.C. 154(b) by 505 days.

(21) Appl. No.: 13/956,511

(22) Filed: Aug. 1, 2013

(65) Prior Publication Data

US 2014/0039161 A1 Feb. 6, 2014

(30) Foreign Application Priority Data

Aug. 1, 2012 (TW) .............. 101127743 A

(51) Int. Cl.
*C07K 1/14* (2006.01)
*C07K 1/30* (2006.01)
*C07K 16/02* (2006.01)

(52) U.S. Cl.
CPC ............... *C07K 16/02* (2013.01); *C07K 1/14* (2013.01); *C07K 1/145* (2013.01); *C07K 1/30* (2013.01); *C07K 1/303* (2013.01)

(58) Field of Classification Search
None
See application file for complete search history.

(56) References Cited

FOREIGN PATENT DOCUMENTS

| CN | 1439650 A | | 9/2003 |
|---|---|---|---|
| CN | 1935841 A | | 3/2007 |
| CN | 101787080 A | * | 7/2010 |
| CN | 101838322 A | | 9/2010 |
| CN | 101955532 A | * | 1/2011 |
| CN | 102276720 A | | 12/2011 |

OTHER PUBLICATIONS

Tan et al., "A novel, cost-effective and efficient chicken egg IgY purification procedure", Journal of Immunological Methods, 2012, doi:10.1016/j.jim.2012.03.003, pp. 1-4.
Akita et al., "Immunoglobulins from Egg Yolk: Isolation and Purification", Journal of Food Science, 1992, vol. 57, No. 3, pp. 629-634.

* cited by examiner

*Primary Examiner* — Daniel E Kolker
*Assistant Examiner* — James Rogers
(74) *Attorney, Agent, or Firm* — Bacon & Thomas, PLLC

(57) ABSTRACT

A method for extracting IgY (γ-livetin) from yolk is disclosed, which comprises the following steps: (A) providing a buffer solution, a yolk sample, and an inorganic salt solution; (B) diluting the yolk sample with the buffer solution to obtain a mixture, stirring the mixture for a predetermined time, and performing a centrifugation on the mixture to obtain a supernatant; and (C) adding the inorganic salt solution into the supernatant to salt out IgY, wherein a pH value of the buffer solution is in a range from 4.6 to 5.4, a salt concentration of the buffer solution is in a range from 0.05 M to 0.15 M, and a saturation degree of the inorganic salt solution is in a range from 30% to 60%.

10 Claims, 4 Drawing Sheets

METHOD FOR EXTRACTING IGY (γ-LIVETIN) FROM EGG YOLK

CROSS REFERENCE TO RELATED APPLICATION

This application claims the benefits of the Taiwan Patent Application Serial Number 101127743, filed on Aug. 1, 2012, the subject matter of which is incorporated herein by reference.

BACKGROUND OF THE INVENTION

1. Field of the Invention

The present invention relates to a method for extracting IgY (γ-livetin) from egg yolk and, more particularly, to an easy and quick method for extracting IgY from egg yolk.

2. Description of Related Art

When invaded by foreign antigens, the immune systems of vertebrate animals often counteract by synthesis and secretion of antibodies (Abs) interacting with the various epitopes of specific antigens. The collection of these Abs are known as polyclonal antibodies (PAb). Since PAb could bind to their antigens with specificity and high affinity, they are widely applied in basic researches, immunodiagnostic, and immunotherapy.

Traditionally, PAb are produced using bigger mammals, e.g., rabbits and goats, for most of the secreted Abs are distributed in the blood and larger quantities of blood are attainable from these animals. However, there are disadvantages for this traditional way of PAb production, such as the needs of larger space and higher cost for keeping animals and the ineffectiveness in producing Abs against conserved mammalian antigens due to the phylogenetic closeness within mammals. Moreover, because mammalian Abs might interact with human's complement system and rheumatoid factors, the applications of these Abs in serological tests of human samples could encounter unnecessary interference. Furthermore, the repeated and invasive animal bleeding manipulation often incurs ethical concerns from the animal welfare groups.

In response to the challenge of foreign antigens, chickens (*Gallus gallus*) also produce antibodies. Unlike in mammals, there are only three classes of antibodies identified in chicken, namely IgM, IgA and IgY. Among them, IgY is the predominant form which is continually synthesized, secreted into the blood and transferred to the egg yolk, where it accumulates to a concentration even higher than that in the blood. It has been reported that a single egg contains as much Abs as an average bleed from a rabbit. Since it is cheaper to feed and house chickens than rabbits and a hen can lay eggs often on a daily basis while a rabbit can not be bled with the same frequency, thus, the use of chicken as immunizing hosts is a much more economical and efficient way to produce PAb than the conventional ways. Other than the economical advantage, chickens are not mammals and therefore are more apt to generate Abs against mammalian antigens, including the highly conserved mammalian proteins. Furthermore, IgY will not interact with mammalian's complement system and rheumatoid factors and consequently, the problem of assay interference can be minimized when using IgY in the serological tests of human samples. Other than the advantages described above, PAb production in chicken offers greater compatibility with animal protection regulations for Abs sampling can be easily achieved by egg collection, rather than by the stressful and invasive bleeding manipulation.

Despite PAb production in chicken offers numerous advantages over the conventional ways, it has not been practiced as popular as it should be. One major reason is that egg yolk contains large amount of lipids (ca. 34% by weight) and other irrelevant proteins and this makes IgY extraction difficult and cumbersome. Furthermore, due to the significant difference between their amino acid compositions, the Protein A/G Sepharose columns commonly used for IgG adsorption is inapplicable for IgY purification. Current protocols of IgY extraction from egg yolk often involve a serial precipitation, chromatographic and ultrafiltration steps, which are complicated and time-consuming. Thus, it is desirable to develop a simple and effective method for extracting yolk IgY to good yield and desired purity.

SUMMARY OF THE INVENTION

The object of the present invention is to provide a method for extracting IgY from egg yolk, so that IgY sample with good yield and high purity can be easily, economically and effectively obtained.

To achieve the object, the method for extracting yolk IgY of the present invention comprises the following steps: (A) providing a buffer solution, a yolk sample, and an inorganic salt solution; (B) diluting the yolk sample with the buffer solution to obtain a mixture, stirring the mixture for a predetermined time, and performing a centrifugation on the mixture to obtain a supernatant; and (C) adding the inorganic salt solution into the supernatant to salt out IgY with improved purity. Herein, a pH value of the buffer solution is in a range from 4.6 to 5.4, a salt concentration of the buffer solution is in a range from 0.05 M to 0.15 M, and a saturation degree of the inorganic salt solution is in a range from 30% to 60%.

In the present invention, the yolk sample is not particularly limited, and can be selected depending on the experimental requirements or the availability of raw material. Preferably, the yolk sample is yolk of a chicken egg, which contains about 100 mg IgY and can be easily available.

In the method for extracting IgY from yolk of the present invention, the salt concentration of the buffer solution can be in a range from 0.05 M to 0.15 M, and preferably is in a range from 0.08 M to 0.12 M. Furthermore, the buffer solution used in the method of the present invention is not particularly limited, and can be an acetate-based buffer solution or a citrate-based buffer solution with pKa of about 5.0. Preferably, the buffer solution used in the method of the present invention is a sodium acetate buffer solution. In addition, the buffer solution having the pH value ranging from 4.6 to 5.4 can remove lipid most effectively. Compared with the conventional acid water method, the buffer solution used in the present invention has better buffering capacity, so the time required to remove yolk lipid can be reduced, the efficiency for extracting IgY can be improved, and the steps for monitoring the pH value of yolk sample can be omitted.

In the step (B) of the present invention, the yolk sample is diluted with the buffer solution in 8-10 folds, but the dilution-fold may be adjusted appropriately based on the experimental conditions. However, the high dilution-fold may cause the subsequent processing works complicated, which would result in a higher purification cost. In addition, the predetermined time for stirring the mixture is 25 min or more; and it indicated that the minimum time required to stir the mixture to fully remove the lipid contained therein is only 25 min in the step (B).

In addition, any salt known in the art, for example, ammonium sulfate, sodium sulfate, and sodium chloride, can be used to prepare the inorganic salt solution of the present invention. Preferably, the inorganic salt solution used in the method of the present invention is an ammonium sulfate solution. During the salting-out process, water molecules absorbed by the inorganic salt hydrate with the inorganic salt molecules to increase the exposed hydrophobic area of the protein, and then the proteins interact with each other via the hydrophobic force thereof and precipitate in the supernatant.

In the case that the saturation degree of the inorganic salt solution is in a range from 30% to 60%, the purity and the yield of the obtained IgY is 50% to 95% and 45% to 98%, respectively. When an inorganic salt solution with 30% saturation degree is used to perform the salting-out process, the obtained IgY has high purity (about 95%) and proper yield (about 45% recovery). When an inorganic salt solution with 60% saturation degree is used to perform the salting-out process, the obtained IgY has proper purity (about 50%) and high yield (about 98%). Hence, an inorganic salt solution with proper saturation degree can be selected according to one's application purposes for the IgY sample. For example, if a high purity preparation of IgY is needed in a short time, an ammonium sulfate solution with 30% saturation degree can be used; or if an antigen-specific IgY preparation is desired, an ammonium sulfate solution with 60% saturation degree can be firstly used to precipitate most IgY, then followed by adsorption to and elution from an antigen affinity column.

Accordingly, in the method for extracting IgY from yolk of the present invention, a sodium acetate solution with a concentration of 0.08-0.12 M and a pH value of 4.6-5.4 can be used as a buffer solution, and a yolk sample can be diluted with the aforementioned buffer solution in 8-10 folds to obtain a mixture. After the obtained mixture is stirred for at least 25 min, solids can be separated from the mixture via a centrifugal force to obtain a supernatant. Then, the ammonium sulfate is added into the obtained supernatant to final 30-60% saturation degree to salt out IgY having a purity of 50-95% and a yield of 45-98%.

In the conventional methods such as PEG precipitation or water dilution method, additional steps have to be performed therewith and long operation time has to be consumed in order to obtain IgY preparation sample having similar purity and yield to that prepared by using the method of the present invention. Recently, a more rapid method has been developed to prepare IgY sample, in which a solution containing gum pectin, κ-carrageenan and $CaCl_2$ is used to remove lipid in the egg yolk, and then a precipitation process is performed on the obtained yolk sample twice with ammonium sulfate solutions with different saturation degrees respectively. After the aforementioned process, 60 mg IgY sample with 80% purity can be obtained from one yolk within 5 hours, and the cost of the reagents is about 5 USD. However, only two processes have to be performed in the method for extracting IgY from yolk of the present invention, in which a sodium acetate buffer solution is firstly used to remove lipid in the yolk sample, and then an ammonium sulfate solution is used to precipitate the IgY protein. The aforementioned process of the method of the present invention only takes 2 hours, and the IgY sample with high purity and yield can be obtained from the yolk. Compared to the aforementioned conventional method, the performing time of the method of the present invention is significantly reduced, and the cost of the reagents used therein is reduced to about 1.5 USD.

In conclusion, the present invention provides a simple and effective method for extracting yolk IgY to high purity and good yield. Furthermore, the cost of the reagents used is inexpensive and no organic solvent is needed in the method of the present invention. Hence, the method of the present invention can be applied to not only the IgY extraction in the lab, but also the large-scale IgY production in the industry field.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
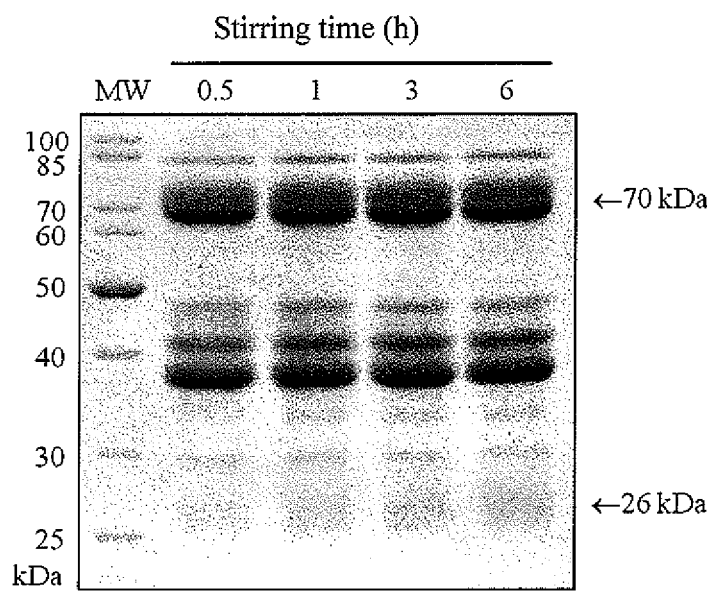
FIG. 1 is an analysis result of SDS-PAGE in Example 1 of the present invention.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Chicken eggs used in the following examples are eggs of White Leghorn laying hens fed in the inventor's lab. Before extracting the IgY, the eggshell was cracked, and the yolk was separated with and placed in a stainless filter. Next, the stainless filter with yolk placed therein was immersed in de-ionized water to remove the remaining egg white on the surface of the yolk. Then, the residual water on the surface of the yolk was absorbed with paper tissues, the yolk membrane was pricked with a dissecting needle, and the yolk liquid was collected in a volumetric cylinder. The volume of the liquid yolk used in the following examples was about 13-15 mL.

In the following examples, Student's T-test was used to determine if results of two different experiments are significantly different from each other. In addition, Analysis Of Variance (ANOVA) was used to determine the difference between multiple experiments. Herein, $p<0.05$ indicates that the observed result has significance.

Example 1—Evaluation the Time Required to Fully Remove Lipid from Yolk to Extract IgY

[Crude Extraction of IgY from Yolk]

Yolk liquid with a predetermined volume was diluted with 0.1 M sodium acetate buffer solution in 9 folds to obtain a mixture. After mixing the mixture well, the mixture was stirred for a predetermined time (stirring time=0.5 h, 1 h, 3 h or 6 h), and solids contained in the mixture were separated therefrom via a centrifugal force at 4° C. (12,000×g, 30 min) to obtain a supernatant, which was a crude extract of the yolk. Then, the volume of the crude extract was measured, a NaN$_3$ solution was added therein to a final concentration of 0.02% (w/v), and the final solution was stored at 4° C. for the subsequent analysis.

[Quantitative Analysis of IgY]

An enzyme-linked immune-sorbent assay (ELSA) was performed to determine the IgY content in the aforementioned crude extract. Briefly, an IgY standard (Jackson, 003-000-003) and the crude extract were diluted with a borate solution (0.2 M) in a serial dilution, and 50 μL of each dilution sample was respectively placed into each well of the ELISA plate (Costar EW-01959-20). After the sample was incubated at room temperature for 6 h or 4° C. overnight, the sample in each well was washed with a wash buffer three times, and then a blocking buffer (180 μL) was added into each well. After the sample was incubated at room temperature for 2 h or 4° C. overnight, the sample in each well was washed with the wash buffer three times, and then rabbit anti-chicken IgY antibodies (Jackson 303-005-00, 1 μg/ml, adding amount=50 μL) was added into each well. After 2 h, the sample in each well was washed with the wash buffer three times, and goat anti-rabbit antibody-alkaline phosphatase (Sigma A3687, 10,000 fold dilution, adding amount=50 μL) was added into each well. After incubated at room temperature for 2 hr, the sample in each well was washed with the wash buffer three times, and then pNPP substrate (adding amount=50 μL) was added into each well. After 30-60 min, the ELISA plate was examined with an ELISA reader (BIO-TEK MQX220) under a wavelength of 405-490 nm to obtain the absorption of each sample (OD$_{405-490}$). Herein, the content of IgY in the crude extract was calculated by comparing the OD$_{405-490}$ thereof with that of the serial diluted IgY standard.

[Quantitative Analysis of Total Proteins]

The total protein content in the crude extract was estimated by Bradford protein assay, and BSA (Sigma A7906) was used as a protein standard herein. Briefly, BSA (2 mg/mL) and the crude extract were serially diluted, and 50 μL of each dilution sample was respectively placed into the wells of a 96-well plate. 200 μL of Bradford reagent was added into each well and incubated for 10 min. Then, the 96-well plate was examined with an ELISA reader (BIO-TEK MQX220) under a wavelength of 595 nm to obtain the absorption of each sample (OD$_{595}$). Herein, the content of total protein in the crude extract was calculated according to the curve obtained from the absorption of the serial diluted BSA standard.

The IgY content and the total protein content extracted from per milliliter of the yolk for four different predetermined times (stirring time=0.5 h, 1 h, 3 h or 6 h) are shown in the following Table 1, in which the IgY contents extracted therefrom were about 6.0-7.2 mg, and the total protein contents extracted therefrom were about 21.7-24.9 mg. After analyzing with ANOVA, there was no statistical difference among the four samples (p>0.05), and this result indicates that only 0.5 h is required to remove lipid completely.

TABLE 1

|  | Stirring time | | | |
| --- | --- | --- | --- | --- |
|  | 0.5 h | 1 h | 3 h | 6 h |
| IgY (mg)/mL yolk | 6.9 ± 2.0 | 7.2 ± 1.7 | 7.2 ± 1.8 | 6.0 ± 1.1 |
| Total protein (mg)/mL yolk | 24.9 ± 1.1 | 22.7 ± 0.9 | 21.7 ± 1.6 | 23.1 ± 1.4 |

[Sodium Dodecyl Sulfate-Polyacrylamide Gel Electrophoresis (SDS-PAGE)]

Proteins (8 μg) was separated by SDS-PAGE with 4% of stacking gel and 12% of separating gel under a provided constant voltage 120V for 2.5 h. After the electrophoresis, the gel was stained with Coomassie blue reagent for at least 1 h, destained with a primary destain buffer for 10-20 min, and then destained with a secondary destain buffer until the protein bands were clearly observed and the background of the gel was transparent.

FIG. 1 is an analysis result of SDS-PAGE, in which the arrows respectively indicate the positions of the H chain (70 kDa) and the L chain (26 kDa) of the IgY protein, and the symbol "MW" represents the protein marker (Bioman, PL01425). As shown in FIG. 1, the species and the contents of the proteins in the four different samples with different stirring time were almost the same. These results indicate that only 0.5 h is required to completely extract proteins from yolk while using the sodium acetate buffer solution as the extraction reagent.

Example 2—Evaluation the pH Value for Extracting IgY from Yolk

Figure 2:
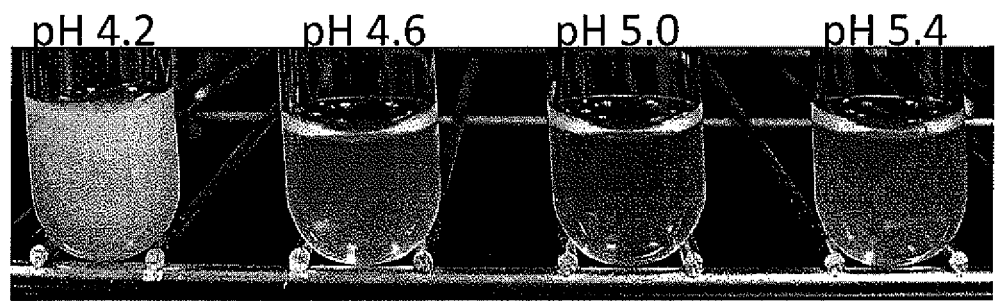
FIG. 2 is a photo showing crude extractions of yolk in Example 2 of the present invention.

In the present example, the process for extracting IgY from yolk is similar to that described in [Crude extraction of IgY from yolk] of Example 1, except that the stirring time used in the present example was 30 min, and 0.1 M sodium acetate buffer solution with different pH value (pH=4.2, 4.6, 5.0, or 5.4) was used in the present example. The appearances of the crude extractions after centrifugation are shown in FIG. 2. As shown in FIG. 2, the appearances of the four crude extractions extracted with the buffer solution having different pH value are significantly different from each other, wherein the crude extraction having the muddiest appearance is the crude extraction extracted with the buffer solution having pH 4.2, the one having the middle clarity is that extracted with the buffer solution having pH 5.4, and the one having the clearest appearance is that extracted with the buffer solution having pH 5.0. Since the clarity of the crude extract is resulted from the content of the water-insoluble lipid, it can be inferred that the lipid-removing effect of the sodium acetate buffer solution is pH-dependent.

In addition, the crude extractions extracted with the buffer solutions having different pH value were also analyzed with the same processes described in [Quantitative analysis of IgY] and [Quantitative analysis of total proteins] of Example 1. As shown in the following Table 2, the IgY contents in the crude extractions extracted with the buffer solutions having different pH value are similar to each other, in which the IgY contents in 10 mL of the crude extractions were about 8.7-9.2 mg. However, the protein contents in the crude extractions are positively correlated with the turbidity of the crude extractions, wherein the protein content was about 63 mg in 10 mL of the muddiest crude extraction extracted with the buffer solution having pH 4.2, and that was about 27.6 mg in 10 mL of the clearest one extracted with that having pH 5.0. In the case that the ratio of the IgY content and the protein content is used to represent the IgY purity in the crude extraction, the IgY purities of the crude extractions extracted with the buffer solutions having different pH values were about 32.6% (pH 5.0), 30.6% (pH 4.6), 21.6% (pH 5.4), and 14.7% (pH 4.2). The statistical analysis results indicate that there is no significant difference between the IgY purities of the crude extractions extracted with the pH 5.0 buffer solution and the pH 4.6 buffer solution, but a significant difference is observed between the crude extractions extracted with the pH 5.4 buffer solution and the pH 4.2 buffer solution.

TABLE 2

| Sodium acetate buffer solution | pH 4.2 | pH 4.6 | pH 5.0 | pH 5.4 |
|---|---|---|---|---|
| IgY (mg)/mL yolk | 9.2 ± 0.7 | 8.7 ± 1.8 | 9.2 ± 1.1 | 8.7 ± 1.9 |
| Total protein (mg)/mL yolk | 63.6 ± 2.2 | 26.4 ± 0.6 | 27.6 ± 2.5 | 39.3 ± 0.7 |
| IgY purity (%) | 14.7 ± 1.1 | 30.6 ± 6.0 | 32.6 ± 2.5 | 21.6 ± 5.1 |

Figure 3:
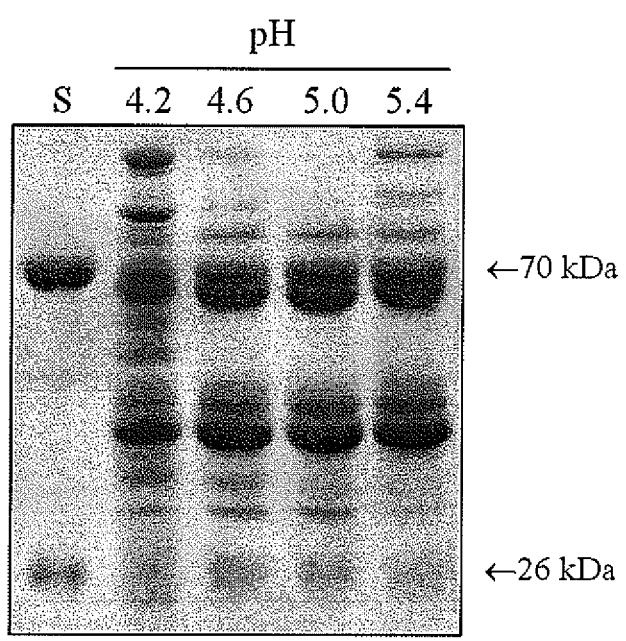
FIG. 3 is an analysis result of SDS gel electrophoresis in Example 2 of the present invention.

Furthermore, the crude extractions extracted with the buffer solutions having different pH value were also analyzed with the same process described in [SDS-PAGE] of Example 1, wherein 12 μg of the proteins from the crude extractions and 3 μg of the IgY standard were respectively loaded into the gel. The results are shown in FIG. 3, wherein the symbol "S" indicates the IgY standard, and the arrows respectively indicate the positions of the H chain (70 kDa) and the L chain (26 kDa) of the IgY protein. On the basis of the equal amount of the loaded proteins, large amounts of different proteins were observed in the crude extraction extracted with the pH 4.2 buffer solution, but small amounts of the IgY protein were observed therein according to the staining densities of the H chain and the L chain thereof. However, decreased amounts of different proteins and increased amounts of the IgY protein were observed in the crude extractions extracted with the pH 5.0 buffer solution and the pH 4.6 buffer solution.

Example 3—Evaluation the Changes of the pH Values of the Crude Extractions

In the present example, three groups were used to understand why the improved efficiency of IgY extraction can be achieved by replacing the conventional acid water with the sodium acetate buffer solution. Herein, the group 1 (sodium acetate group) was prepared by diluting a predetermined amount of yolk with 0.1 M sodium acetate buffer solution (pH 5.0) in 9 folds, and the initial pH value of the diluted sample was 5.1. The group 2 (acid water group) was prepared by diluting the same amount of yolk as that used in the group 1 with deionized water in 9 folds and adding 0.1 N HCl therein (<2 v/v %), and the initial pH value of the sample was 5.0. The group 3 (comparative group) was deionized water added with a little amount of 0.1 N HCl to adjust the pH value thereof was 5.0. The prepared samples of the aforementioned three groups were stirred at 4° C., and the changes of the pH values thereof were observed.

Figure 4:
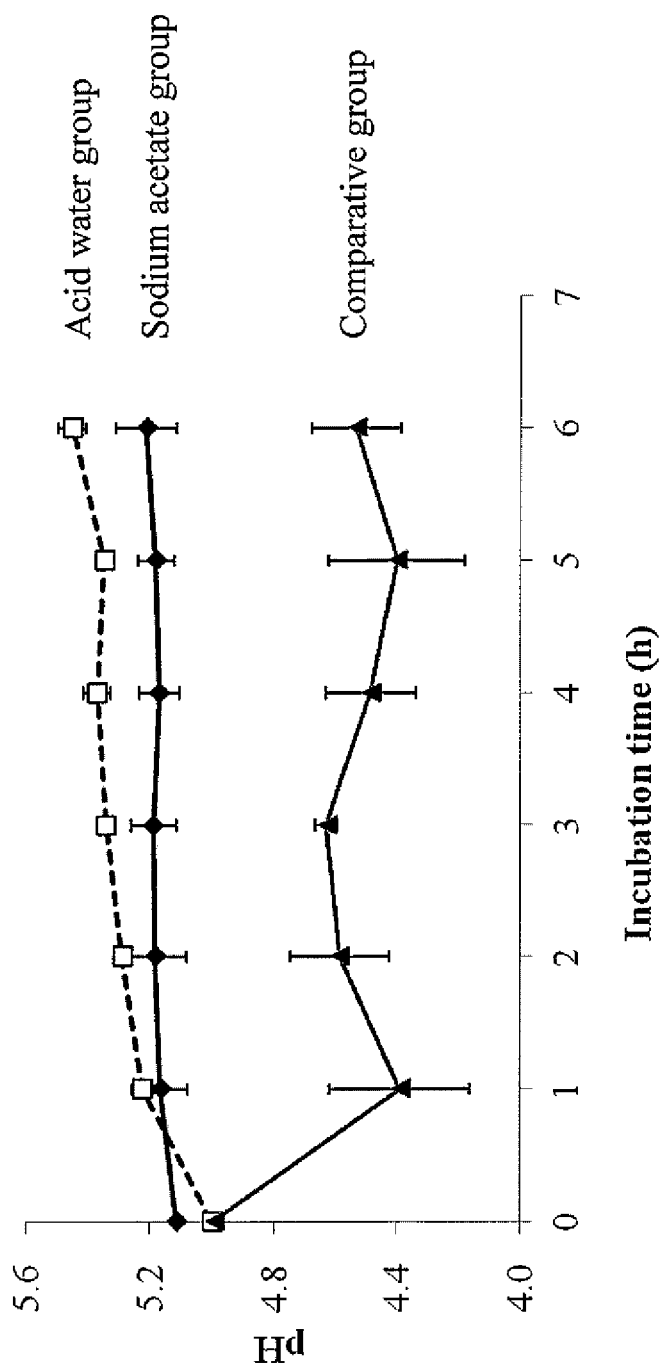
FIG. 4 is a diagram showing the pH changes of the samples in Example 3 of the present invention.

As shown in FIG. 4, the pH value of the sample of the group 1 (sodium acetate group) maintained to be 5.1 within 6 h (incubation time); that of the group 2 (acid water group) gradually increased to 5.4 within 6 h; and that of the group 3 (comparative group) rapidly decreased to 4.4 within 1 hr and maintained to be 4.4 until the experiment was ended.

The rapid decrease of the pH value of the sample of the comparative group (group 3, 5.0→4.4) is most likely resulted from the solution of $CO_2$ in the air. The increases of the pH values of the samples of the sodium acetate group (group 1, 5.0→5.1) and the acid water group (group 2, 5.0→5.4) are probably resulted from that the aggregation of the lipids may consume the $H^+$ ions in the buffer solution or the acid water. Since the sodium acetate solution have buffer capacity to resupply the consumed $H^+$ ions, only a slight increase of the pH value of the sample was observed initially (5.0→5.1), and the pH value thereof can be maintained to be 5.1 until the experiment was ended. However, the acid water does not have buffer capacity and cannot resupply the consumed $H^+$ ions, so the pH value of the sample was gradually increased as the lipids of the yolk aggregated.

According to the aforementioned results, the reaction for removing lipids during the IgY extraction appears to be a pH-dependent reaction, and only a narrow pH range is suitable to remove lipids completely. In addition, the aforementioned results also confirm that $H^+$ ions in the solution are consumed during the IgY extraction. Since the sodium acetate buffer solution has excellent buffer capacity, the pH value during the IgY extraction can be maintained, and therefore the lipids in the yolk can be removed rapidly and effectively. However, the acid water demonstrates poor buffering in the pH range for the IgY extraction, so the effect of removing lipids is not good enough, and a long operation time has to be consumed in order to obtain a sufficient effect of removing lipids.

Example 4—Evaluation the Effect of IgY Precipitation by Using Ammonium Sulfate

[IgY Precipitation by Using Ammonium Sulfate]

Ammonium sulfate (Merk 1.01217) was added into the aforementioned crude extractions from the yolk (10 mL) to 30%, 40%, 50% or 60% saturation. After stirring the mixture at 4° C. for 30 min, the pellet was separated by a centrifuge at 4° C. (12,000×g, 30 min), and then the obtained pellet was re-suspended with 1 mL PBS buffer. The obtained product was analyzed with the same processes described in [Quantitative analysis of IgY] and [Quantitative analysis of total proteins] of Example 1.

As shown in the following Table 3, the precipitation amounts of total proteins and IgY were increased as the saturation of the ammonium sulfate in the crude extractions elevated. When the saturation of the ammonium sulfate in the crude extraction was 30%, 4.9 mg proteins containing 4.4 mg IgY can be precipitated from 10 mL of the crude extraction. When the saturation thereof was 60%, 16.9 mg proteins containing 8.9 mg IgY can be precipitated therefrom. These results indicate that the precipitation amounts of the total proteins and IgY do not change proportionally as the saturation of the ammonium sulfate in the crude extractions elevated. Hence, the adding amount of the ammonium sulfate influences not only the IgY yield but also the IgY purity (IgY/total proteins) obtained from the crude extractions. When the saturation of the ammonium sulfate in the crude extraction was 30%, the IgY purity obtained therefrom was about 90% though the IgY yield obtained therefrom was only about 48%. When the saturation thereof was 60%, the IgY yield obtained therefrom was about 96%, but the IgY purity obtained therefrom was decreased to 53%.

TABLE 3

| | Yolk (mL) | Saturation of ammonium sulfate in crude extract | | | |
| | | 30% | 40% | 50% | 60% |
|---|---|---|---|---|---|
| Total protein content (mg) (Yield, %) | 28.3 ± 1.2 (100%) | 4.9 ± 0.7 (17%) | 7.6 ± 0.3 (27%) | 12.6 ± 0.6 (45%) | 16.9 ± 1.6 (60%) |

TABLE 3-continued

| | Yolk (mL) | Saturation of ammonium sulfate in crude extract | | | |
| --- | --- | --- | --- | --- | --- |
| | | 30% | 40% | 50% | 60% |
| IgY content (mg) (Yield, %) | 9.2 ± 0.7 (100%) | 4.4 ± 0.6 (48%) | 6.3 ± 0.8 (69%) | 8.3 ± 0.4 (90%) | 8.9 ± 0.6 (96%) |
| IgY purity (%) | 32.5 ± 1.9 | 89.7 ± 2.1 | 82.8 ± 7.2 | 65.8 ± 4.0 | 53.1 ± 6.5 |

Figure 5:
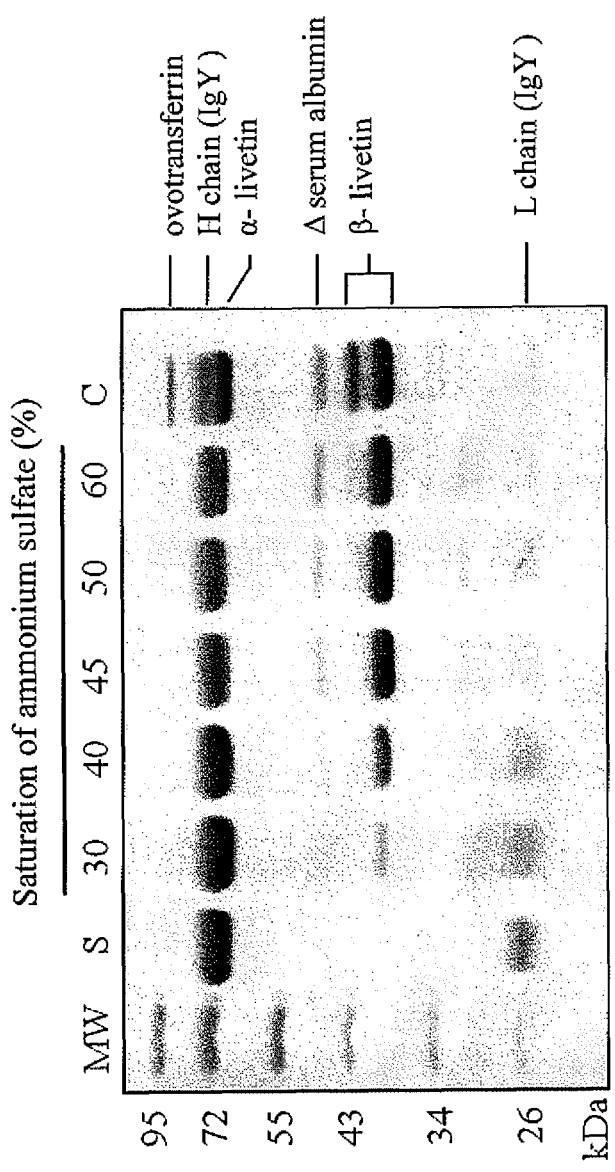
FIG. 5 is an analysis result of SDS gel electrophoresis in Example 4 of the present invention.

Furthermore, the obtained products obtained by salting out with ammonium sulfate in different saturations were also analyzed with the same process described in [SDS-PAGE] of Example 1, wherein 3 μg of the proteins from the products were respectively loaded into the gel. The results are shown in FIG. 5, in which the symbol "S" indicates the IgY standard (Jackson, 003-000-003), the arrows respectively indicate the positions of the H chain (70 kDa) and the L chain (26 kDa) of the IgY protein, and the symbol "MW" indicates the protein marker. From the result shown in FIG. 5, the highest IgY purity can be obtained when using ammonium sulfate in 30% saturation, and only few amounts of β-livetin and Δ serum albumin were observed. As the saturation of ammonium sulfate in the crude extraction elevated, the species of the proteins increased, and the obtained IgY purity decreased. This result is consistent with those shown in Table 3.

In conclusion, the sodium acetate buffer solution (especially, 0.1 M and pH 5.0) shows excellent effect of removing lipids in the yolk, and only 0.5 h has to be taken to obtain a crude extract containing more than 30% IgY, compared to the conventional method in which at least 5.5 h has to be taken by using acid water. Based upon our experience, the crude extract prepared by using the present invention is good enough for various immunochemical applications such as Western Blot and ELISA. In addition, according to the IgY precipitation results, the IgY yields obtained from the crude extraction were about 48%, 69%, 90% and 96%, and the IgY purities obtained therefrom were about 90%, 83%, 66% and 53%, when the saturations of the ammonium sulfate added in the crude extractions were 30%, 40%, 50% and 60% respectively. These results can be used as a reference for the IgY yield and the IgY purity, in order to select suitable amounts of ammonium sulfate to precipitate IgY from the crude extractions for the further applications.

Although the present invention has been explained in relation to its preferred embodiment, it is to be understood that many other possible modifications and variations can be made without departing from the spirit and scope of the invention as hereinafter claimed.

What is claimed is:

1. A method for extracting γ-livetin (IgY) from yolk, consisting of the following steps:
   (A) providing a buffer solution, a yolk sample, and an inorganic salt solution;
   (B) diluting the yolk sample with the buffer solution to obtain a mixture, stirring the mixture for a predetermined time, and performing a centrifugation on the mixture to obtain a supernatant; and
   (C) adding the inorganic salt solution into the supernatant to salt out IgY,
   wherein a pH value of the buffer solution is in a range from 4.6 to 5.4, a salt concentration of the buffer solution is in a range from 0.05 M to 0.15 M, the predetermined time for stirring the mixture is 25 min or more, and a saturation degree of the inorganic salt solution is in a range from 30% to 60%.

2. The method as claimed in claim 1, wherein the yolk sample is yolk of a chicken egg.

3. The method as claimed in claim 1, wherein the salt concentration of the buffer solution is in a range from 0.08 M to 0.12 M.

4. The method as claimed in claim 1, wherein the buffer solution is an acetate-based buffer solution or a citrate-based buffer solution.

5. The method as claimed in claim 4, wherein the buffer solution is a sodium acetate buffer solution.

6. The method as claimed in claim 1, wherein the yolk sample is diluted with the buffer solution in 8-10 folds in the step (B).

7. The method as claimed in claim 1, wherein the inorganic salt solution is an ammonium sulfate solution.

8. The method as claimed in claim 1, wherein the IgY obtained in the step (C) has a purity of 50% to 95%.

9. The method as claimed in claim 1, wherein the IgY obtained in the step (C) has a yield of 45% to 98%.

10. The method as claimed in claim 1, wherein the yolk sample is yolk of a chicken egg; the salt concentration of the buffer solution is in a range from 0.08 M to 0.12 M; the buffer solution is a sodium acetate buffer solution; the yolk sample is diluted with the buffer solution in 8-10 folds in step (B); the predetermined time for stirring the mixture is 25 min or more; and the inorganic salt solution is an ammonium sulfate solution.

* * * * *